United States Patent [19]
Slater et al.

[11] Patent Number: 5,452,335
[45] Date of Patent: Sep. 19, 1995

[54] TEMPERATURE CYCLE COUNTER

[75] Inventors: Charles R. Slater, Fort Lauderdale; Thomas O. Bales, Miami; Jurgen A. Kortenbach, Miami Springs; George Nunez; David Turkel, both of Miami, all of Fla.; David P. Gordon, Stamford, Conn.

[73] Assignee: Symbiosis Corporation, Miami, Fla.

[21] Appl. No.: 999,228

[22] Filed: Dec. 31, 1992

[51] Int. Cl.$^6$ ............................................. G01K 1/02
[52] U.S. Cl. ............................................. 377/25
[58] Field of Search ............................................. 377/65

[56] References Cited

U.S. PATENT DOCUMENTS

| | | | |
|---|---|---|---|
| 987,273 | 3/1891 | Wardwell | 235/91 R |
| 1,469,552 | 10/1923 | Burdette | 235/91 R |
| 1,657,828 | 1/1928 | Henderson | 74/128 |
| 2,359,661 | 10/1944 | Moody | 235/121 |
| 2,382,708 | 10/1945 | Graydon, Jr. et al. | 235/131 |
| 2,476,560 | 7/1949 | Norgard | 235/117 |
| 2,762,567 | 9/1956 | Van Veen | 235/132 |
| 2,996,241 | 8/1961 | Hoffmann | 235/1 |
| 3,138,030 | 6/1964 | Godel | 74/159 |
| 3,178,109 | 4/1965 | Farrell et al. | 235/91 |
| 3,428,324 | 2/1969 | Weisbecker | 273/153 |
| 3,713,582 | 1/1973 | Furuoka | 235/116 |
| 3,720,898 | 3/1973 | Levinn | 337/95 |
| 4,382,063 | 5/1983 | Romito et al. | 422/57 |
| 5,090,033 | 2/1992 | Murray-Shelley | 377/28 |
| 5,143,453 | 9/1992 | Weynant née Girones | 374/205 |

FOREIGN PATENT DOCUMENTS

| | | | |
|---|---|---|---|
| 581400 | 2/1994 | European Pat. Off. | G06M 1/08 |
| 0207224 | 10/1939 | Germany . | |

Primary Examiner—Margaret R. Wambach
Attorney, Agent, or Firm—David P. Gordon

[57] ABSTRACT

An apparatus for counting the number of times a temperature cycle occurs includes an indicator having sequential indicia and a temperature responsive member for indicating a next one of the indicia. Mechanical, fluid mechanical and electronic versions of the invention are disclosed. In the mechanical version, the indicator can be a ratchet member having teeth, a pawl and a display surface containing indicia. A temperature responsive element such as a bimetallic member engages the teeth of the ratchet and advances the ratchet each time the apparatus is subjected to a preset temperature cycle. A housing with a window masks the display to indicate one of the indicia as advanced by the temperature responsive element. Preferred embodiments of the mechanical version include a ring-like ratchet member with interior teeth and an exterior display surface. The number of teeth is preferably one or more less than the number of indicia so that upon advancing the ratchet member to the last indicia, it can be advanced no further. The bimetallic element is mounted inside the ring and the housing covers the outer surface of the ring. A removable locking pin is provided to prevent movement of the ratchet member until activated.

49 Claims, 6 Drawing Sheets

TEMPERATURE CYCLE COUNTER

This invention relates to a temperature cycle counter. More specifically, the invention relates to a device for registering the number of times ambient temperature has exceeded a preset value.

BACKGROUND OF THE INVENTION

Many perishable goods such as food, drugs and cosmetics can be damaged by exposure to heat. Similarly, other products are damaged by exposure to extreme cold. Generally, these goods can be stored and transported safely only if the ambient temperature is kept within a specified range. Some products may tolerate a few exposures to extreme temperature, but after repeated exposures to such temperatures the product will be damaged. In addition to food, drugs and cosmetics, other products which can be damaged by extreme temperatures include film, electronics, plastics, various synthetics, and chemicals. Moreover, while perhaps not damaged, some products, for example chocolates and certain frozen goods, can be unfavorably altered by exposure to extreme temperatures. It is therefore desirable to keep track of changes in ambient temperature so that it will be known whether these goods are damaged or altered. Unfortunately, while it is well known to maintain a constant temperature in a storage or transport facility, it is extremely difficult to know with certainty all of the places a particular package of temperature sensitive goods has been during the course of storage and shipment. It is possible that during transportation from one storage facility to another, temperature sensitive goods are exposed to extreme temperature even if best efforts have been made to assure constant temperatures at storage facilities.

SUMMARY OF THE INVENTION

It is therefore an object of the invention to provide an automatic mechanism for tracking the number of times a preset high and/or a preset low temperature has been reached.

It is also an object of the invention to provide a counter mechanism which is integral with the packaging of temperature sensitive goods so that the packaging itself will display the number of times it has been exposed to a preset high and/or low temperature.

It is a further object of the invention to provide a mechanism by which the counter is activated but which will not allow the counter to be deactivated after its initial activation.

It is yet another object of the invention to provide a temperature cycle counter which will count up to a preset number and not repeat.

In accord with the aforestated objects of the invention, the temperature cycle counter broadly comprises an indicator attached to the surgical instrument where the indicator has a predetermined plurality of sequential indicia, and heat responsive means for indicating a next one of the indicia when the counter has reached a preset temperature or when a temperature cycle has been detected. Typically, the counter is provided with a display window and at least a portion of the heat responsive means is viewable through the display window. Also, the cycle indicator typically incrementally advances each time the counter has reached a preset temperature or has gone through a temperature cycle. The preferred heat responsive means mechanism is a curved bimetallic pawl Which expands and contracts with changes in temperature, although other mechanical, chemical, fluid, electrical, or combination mechanisms may be utilized. By arranging the indicator as a ratchet member with a plurality of teeth and an outside display surface, the curved bimetallic pawl or other heat responsive means can expand over a ratchet tooth as the counter and bimetallic pawl are heated, and then catch behind the tooth and advance the ratchet as the instrument and bimetallic pawl cool. Alternatively, the curved bimetallic pawl or other heat responsive means can be arranged so that it expands behind the tooth and advances the ratchet as the counter and bimetallic pawl are heated, and then contracts over a ratchet tooth as the instrument and bimetallic pawl cool. As the ratchet is advanced, the outside display surface of the ratchet moves past the window in the instrument and displays a new use indication or incremental number. To prevent backward movement of the ratchet member, a second pawl is preferably provided which allows movement of the ratchet member in one direction only.

Preferred aspects of the ratchet member embodiment of the invention include: arranging the teeth of the ratchet so that once the counter has reached its maximum value, no further activation is possible; providing a locking pin to prevent operation of the counter until activated; and providing the counter as part of packaging for temperature sensitive goods.

Heat responsive mechanisms other than bimetallic strips which may be used in conjunction with a ratchet or the like are also disclosed. One such mechanism is a wax-filled cylinder and piston arrangement whereby the wax expands when melting and contracts when solidifying in order to move the piston. Another such mechanism is a gas-filled aneroid bellows which expands when heated and contracts when cooled in order to move a piston.

Other cycle counters employing heat responsive means which do not use a ratchet mechanism are also disclosed. For example, one cycle counter includes a source reservoir containing a colored fluid, a first one-way valve, a reservoir/pump, a second one-way valve, and a single conduit connecting to a plurality of fluid containers. As the cycle counter is heated, the pump (e.g., wax plug) of the reservoir/pump expands and forces fluid contained in the reservoir through the second one-way valve into the first fluid container; thereby indicating a first use. When the use indicator cools, the wax pump contracts, and would leave a vacuum in the reservoir above the pump if not for the source reservoir. Thus, upon cooling, fluid is drawn into the reservoir/pump through the first one-way valve. Upon a second heating of the cycle counter, these actions are repeated except that now that the first fluid container is full, and the fluid is forced to flow along the conduit to the next fluid container to indicate a second use.

In accord with another aspect of the invention, an electronic cycle counter is disclosed. The electronic cycle counter comprises one of any of a number of electronic displays such as LCD or LED devices which is coupled to an electronic counter which may be an integrated circuit and an electronic sensor such as a thermistor, diode, transistor, or the like. A preferred embodiment of the electronic cycle counter includes a substantially cylindrical package containing an LCD display on its round face, a cylindrical circuit board placed behind the display and a cylindrical power cell placed behind the circuit board. The power cell is preferably a "coin cell" such as the type used in electronic watches and the entire use counter package is approximately twice the size of the power cell.

Preferred aspects of the electronic cycle counter include: arranging the circuit and sensor so that the display count is incremented only after the device has been exposed to a temperature cycle; i.e., from a first preset high or low temperature to a second preset low or high temperature, and back to the first preset high or low temperature; cooled back to the preset low temperature (i.e. one "temperature excursion"); alternatively arranging the circuit and sensor so that the display counter is incremented based on the length of time the device has been exposed to a threshold temperature; and as a further alternative, arranging the circuit and sensor so that the display counter is incremented both based on the length of time the device has been exposed to a threshold temperature and the amount above or below the threshold temperature the device is subjected. The last alternative is particularly advantageous for use with shipments of perishables such as milk, where the milk will spoil based both on the temperature reached, and the length of time the milk is subjected to the elevated temperatures.

Additional objects and advantages of the invention will become apparent to those skilled in the art upon reference to the detailed description taken in conjunction with the provided figures.

BRIEF DESCRIPTION OF THE DRAWINGS

FIG. 4b is a side elevation view of the embodiment of FIG. 4a;

FIG. 5 is a side elevation view of yet another embodiment of ratchet wheel;

FIG. 6 is a side elevation schematic view of a melting-wax actuator;

DETAILED DESCRIPTION OF THE PREFERRED EMBODIMENTS

Figure 1:
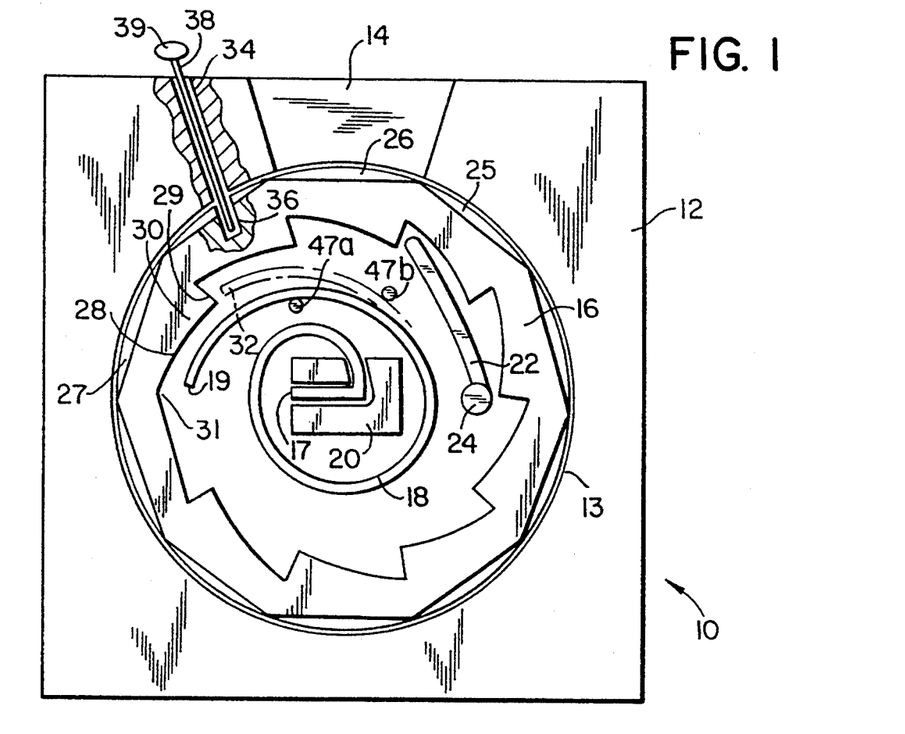
FIG. 1 is a side elevation view in partial cross section of a first embodiment of the temperature cycle counter invention.
Figure 2:
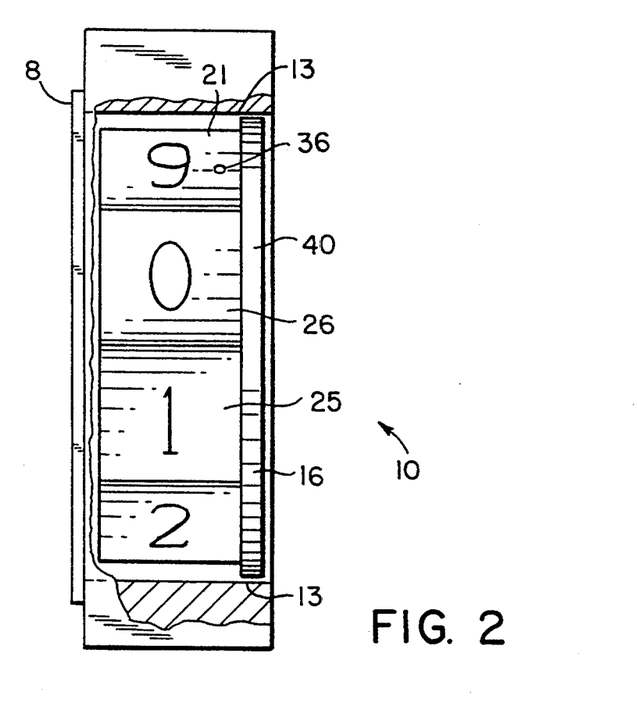
FIG. 2 is a side elevation view of the ratchet wheel of FIG. 1.

Referring now to FIGS. 1 and 2, a temperature cycle counter 10 according to a first preferred embodiment invention is seen and includes a housing 12 having a generally cylindrical orifice 13, a window 14, and a rotatable ratchet wheel 16 visible through a window 14. The ratchet wheel 16 is formed as a ring with a plurality of interior teeth 30 having sloping surfaces 28, and back shoulders 29. The outer circumference of the wheel 16 is provided with a plurality of incremental indicia such as sequentially numbered facets 26. The number of interior teeth 30 is preferably one less than the number of numbered facets 26 and each facet 26 but for one 27 corresponds to an interior tooth 30. The wheel 16 is also provided with an engaging rim 40 which rotatably engages the cylindrical orifice 13 of housing 12. In order to advance the ratchet wheel 16, a bimetallic spiral 18 is provided and is anchored at one end 17 in a centrally located anchor 20 which forms part of the housing 12.

The bimetallic spiral 18 is chosen and designed so that it expands (i.e., the spiral widens) a predetermined amount when it is subjected to a predetermined first temperature. For example, bimetallic spiral 18 in FIG. 1 is chosen to expand sufficiently at a first temperature so that its free end 19 moves in a clockwise direction to the position 32 shown in phantom in FIG. 1. Of course, upon cooling to its original temperature, the bimetallic spiral returns to its original position shown in FIG. 1. It will thus be appreciated by those skilled in the art that when the counter 10 is subjected to a temperature cycle (original temperature to threshold first temperature and back) the bimetallic spiral 18 will expand, and possibly ride over a sloping surface 28, and then snap behind a shoulder 29 of a tooth 30 of the wheel 16. If the spiral 18 contacts the sloping surface 28 as it expands, wheel 16 will not be moved in the clockwise direction, because a second pawl 22 is provided to prevent such clockwise rotation. As seen in FIG. 1, pawl 22 is mounted by a pin 24 to the housing 12 between the spiral 18 and the toothed interior of wheel 16 so that it is biased towards and will engage the shoulder 29 of a tooth 30 of the ratchet. Thus, as ratchet wheel 16 rotates counterclockwise, pawl 22 rides along the sloped surface 28 and falls behind shoulder 29. However, if the wheel 16 starts rotating clockwise, pawl 22 jams into the shoulder 29 and prevents it from doing so.

As aforementioned, when the bimetallic spiral is heated, it expands and causes its free end 19 to fall behind a tooth shoulder 29. However, when the counter (and bimetallic spiral) cools, the spiral 18 will attempt to return to its original position. Because the free end 19 of the bimetallic spiral is located behind the tooth shoulder 29, upon cooling, the bimetallic spiral acts on the tooth shoulder and thereby rotates wheel 16 in a counter clockwise direction. By carefully dimensioning the spiral 18 and by providing each facet with a corresponding tooth 30, the wheel 16 will be rotated one facet each time the counter is heated or heated and then cooled. If desired, in order to reduce criticality in dimensioning, limiters or stops 47a and 47b can be provided. Limiter 47a which is located between the hub 20 and the outer portion of bimetallic strip 18 limits the coiling motion of the bimetallic spiral as it cools, thereby preventing the bimetallic strip from pushing the ratchet wheel 16 too far forward. Limiter 47b, on the other hand, is located between the bimetallic strip 18 and the ratchet wheel 16, and limits the opening of the bimetallic spiral as it heats, thereby preventing the free end 19 of the bimetallic strip from moving too far backward (e.g., behind two or more teeth).

Because the use counter uses a rotating wheel, it is desirable that the counter should stop advancing after it has advanced to the last facet or indication, and before it recycles to the first facet or indication. Thus, the counter should ideally advance from a starting position, for example where the numeral zero of a facet 26 is shown through window 14, to a position where the numeral one of a facet 25 is seen through window 14, and so on until a last facet 21 which indicates the maximum number is exposed through window 14. At that point, the ratchet wheel should advance no further. In order to prevent the ratchet wheel from further advancement (i.e., to the position showing numeral zero again), a shallow surface 31 is provided adjacent facet 27 in place of a tooth 30 to prevent the wheel 16 from being rotated beyond the position where facet 21 is exposed through window 14. Thus, when the last facet indicating the highest number is exposed through window 14, the shallow surface 31 assumes a position relative to the free end 19 of bimetallic spiral 18 such that there is no tooth shoulder which free end 19 can engage when spiral 18 expands.

The counter 10 may be affixed to temperature sensvie goods or packaging containing such goods by a self-adhesive peel-and-stick strip 8 or similar devices. Once the counter is so affixed, it is activated by pulling ring 39 to remove locking pin 38. The locking pin 38 is shown extending through and received by a bore 34 in the housing, and ratchet wheel 16 is preferably further provided with a locking bore 36, for example as shown in facet 21 which receives the pin 38. When in place, pin 38 prevents advancement of the wheel 16. Preferably, the locking pin cannot be resinserted after the ratchet wheel has advanced.

Figure 3:
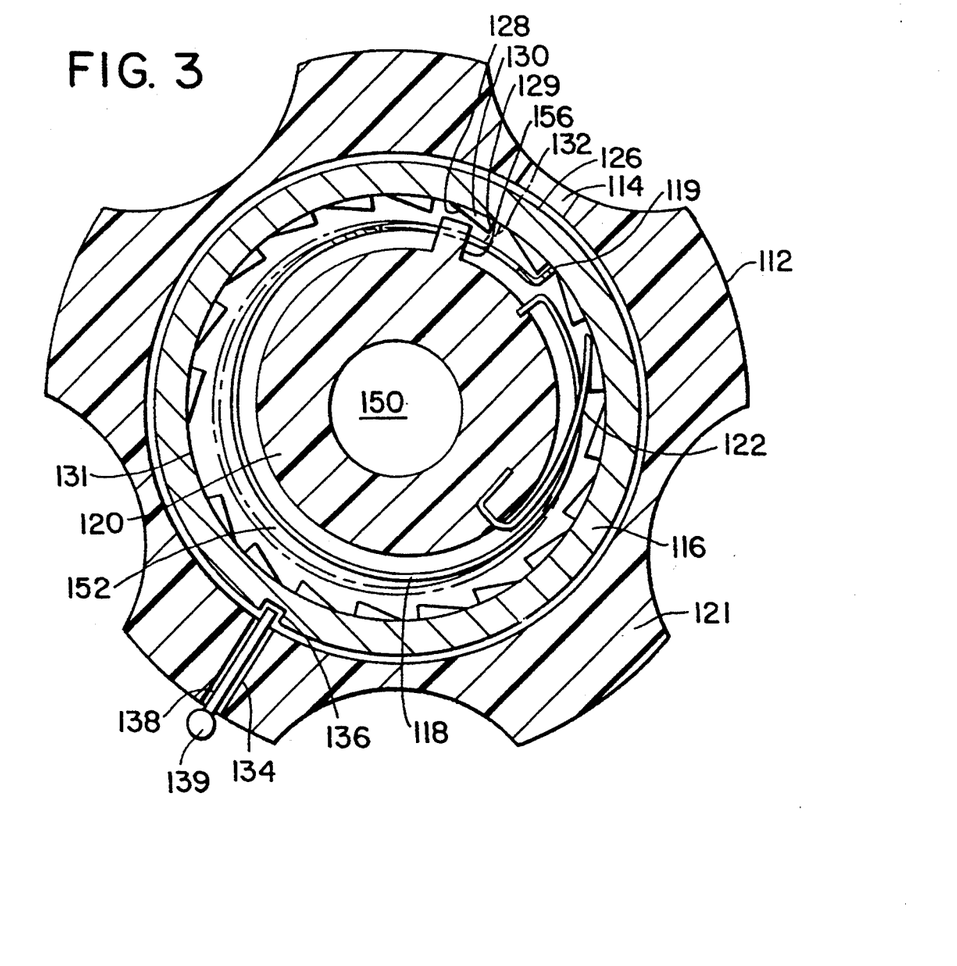
FIG. 3 is a cross sectional view of a second embodiment of the use counter invention.
Figure 3A:
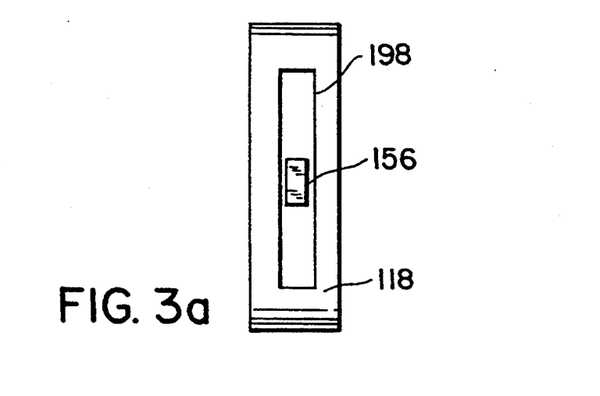
FIG. 3a is a close detail of the bimetallic ring and guide boss.

Turning now to FIG. 3, a second embodiment of the invention is shown. Here the counter 100 of the invention is built within a ferrule 112 having a central bore 150. A window 114 and a radial locking pin bore 134 serve the same functions as the window 14 and bore 34 in the embodiment of FIG. 1. A ratchet wheel 116 in the form of a ring is mounted coaxially within the ferrule 112 and rotatable with respect to it. The ratchet wheel 116 is provided with a plurality of interior teeth 130 with sloping surfaces 128 and shoulders 129, and the outer surface of the wheel 116 is provided with incremental indicia 126. The number of teeth 130 is preferably chosen to be one less than the number of indicia 126 for the same reason as stated above with reference to FIG. 1. A bimetallic ring 118 which acts as a pawl for the ratchet wheel 116 is mounted at one end 117 in a hub 120 of the ferrule 112. Hub 120 is preferably eccentrically located relative to the outer portion 121 of the ferrule 112. The hub 120 surrounds central bore 150 through which the counter may be attached to temperature sensitive goods or packaging containing such goods. As shown in FIG. 3, the bimetallic ring 118 surrounds almost 360° of the hub 120 so that its bent end 119 engages the shoulder 129 of a tooth 130 in the vicinity of its mounted end 117. In order to hold, guide, and limit the movement of the bimetallic ring 118, a movement limiting guide boss 156 is provided on the hub 120 near the bent end 119 of the bimetallic ring 118. A detailed view of guide boss 156 is shown in FIG. 3a where it can be seen that the bimetallic ring 118 is provided with a slot 198 into which boss 156 extends. Expansion and contraction of the ring 118 is thereby limited by the boss 156 as it engages the edges of slot 198. A second pawl 122 is also mounted in the hub 120 and functions substantially the same way as pawl 22 described above with reference to FIG. 1.

Bimetallic ring 118 preferably is chosen to expand a predetermined amount at a predetermined temperature as was described above with reference to the bimetallic spiral 18 of FIG. 1. In this second embodiment, however, as ring 118 expands, its bent end 119 moves forward (counterclockwise) in the limiting guide boss 156 as shown in phantom. In this manner, as the bimetallic ring heats up, it advances the wheel 116 counterclockwise with the end of the ring as shown at 132 pushing the tooth 130 forward. When the ring cools and compresses, the bent end 119 of the bimetallic ring 118 rides up over the ramped surface 128 of the tooth 130 until it falls behind the shoulder 129 and returns to its original position now behind a clockwise adjacent tooth 130. As the bent end 119 of ring 118 rides up over the ramped surface 128 of the tooth 130, the wheel is prevented from rotating clockwise because of the action of pawl 122.

The hub 120 of ferrule 112 is preferably located in an eccentric manner relative to central bore 150 so that a larger space 152 lies between it and the interior of wheel 116 at a point approximately 180+ from the point where mounted end 117 of ring 118 is secured in hub 120. This space provides room for the expansion of ring 118.

As with the embodiment of FIG. 1, a shallow surface 131 is provided at a preselected position in place of a tooth 130. The shallow surface 131 prevents the wheel 116 from being rotated beyond the position where the last use indicia is exposed through window 114.

For the same reasons as mentioned above regarding the embodiment of FIG. 1, counter 100 is also preferably provided with a locking pin 138 which is received by bore 134 in ferrule 112 and in bore 136 in wheel 116. The locking pin 138 prevents movement of the wheel until activated by pulling on pull ring 139.

Figure 4:
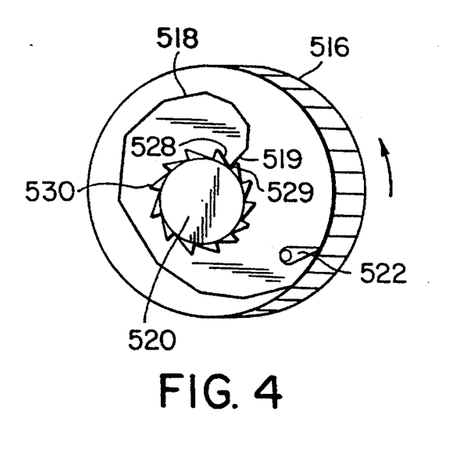
FIG. 4 is a side elevation of an alternate embodiment of ratchet wheel and bimetallic pawl.

Turning now to FIG. 4, an alternate embodiment of a ratchet wheel and bimetallic pawl is shown. Here the ratchet wheel 520 is centrally located with exterior teeth 530, and the bimetallic pawl 518 engages the teeth 530 of the ratchet from the outside. As shown in FIG. 4, the bimetallic pawl 518 is coupled to the rotating display member 516 while the ratchet wheel 520 remains stationary. A direction limiting pawl 522 engages the rotating member 516 so that it can be advanced in one direction only as indicated by the arrow; in this case counterclockwise. As the bimetallic pawl 518 expands when heated, its free end 519 presses against shoulder 529 of a tooth 530 thereby advancing the rotating display member 516 in a counterclockwise direction. The dimensions of the pawl 518 are chosen so that its expansion advances the display member 516 a predetermined amount. When the bimetallic pawl 518 cools, it contracts, and its free end 519 slides up over the sloping surface 528 of a next tooth 530 to rest against a next shoulder 529. In this manner, the bimetallic pawl 518 is ready to advance the display member again when heated. The similarities and differences between this embodiment and the embodiments described above with reference to FIGS. 1–3 will now be apparent to those skilled in the art. For simplicity, some of the similar features of this embodiment have not been shown in the drawing, but it will be appreciated that a window, locking pin, missing tooth, etc. can and would be applied to this embodiment as well.

Figure 4A:
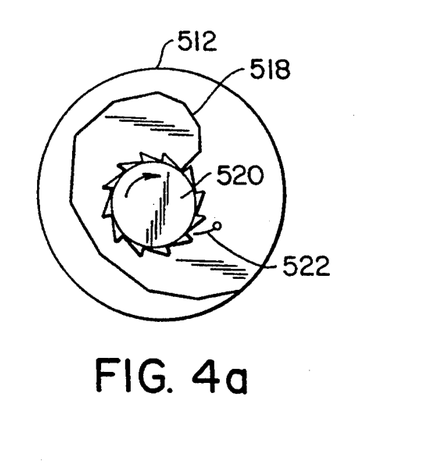
FIG. 4a is a view similar to FIG. 4 but of an alternate embodiment.
Figures 4B, 5, 6:
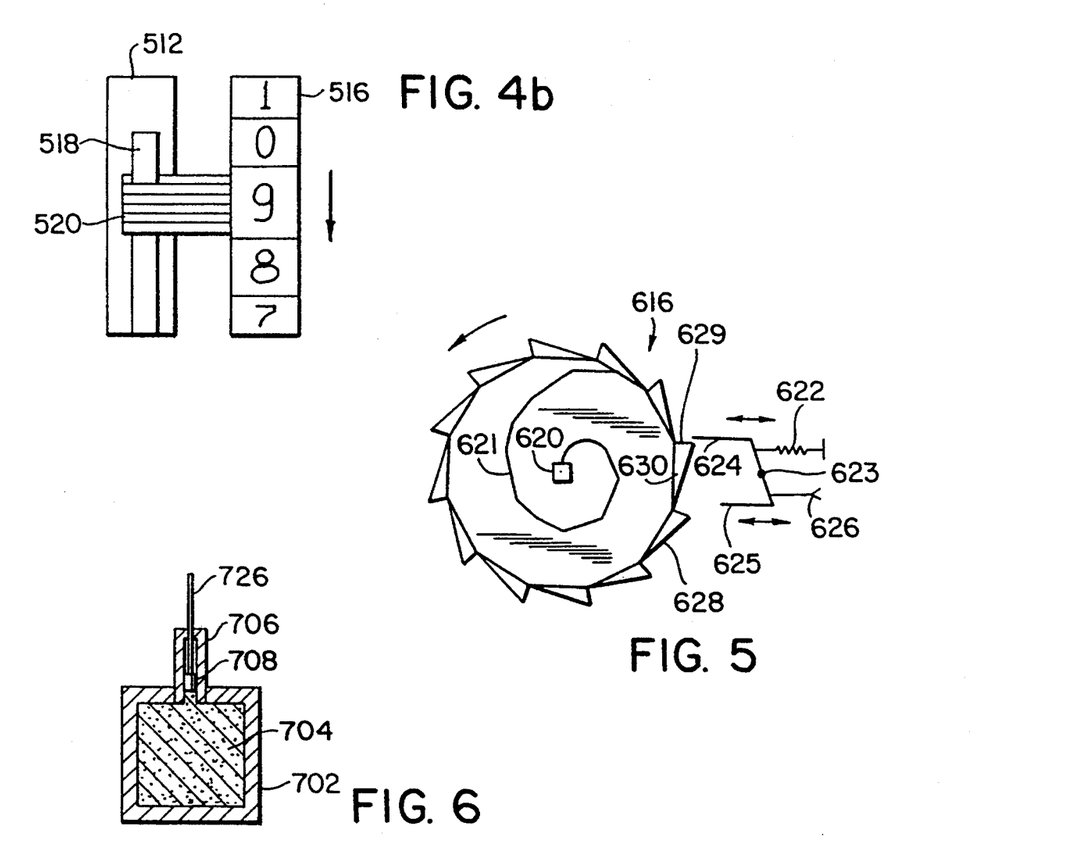

FIGS. 4a and 4b show an embodiment similar to the embodiment of FIG. 4, but here the centrally located ratchet wheel 520 is not stationary and is laterally coupled to a display wheel 516 as seen in FIG. 4b, and the bimetallic pawl 518 is coupled to a fixed outer housing 512. Direction limiting pawl 522 engages the teeth of the ratchet wheel 520 so that incremental movement of the display means 516 is in the clockwise direction as shown. When the bimetallic pawl 518 is heated, its free end rides over a tooth; while when the bimetallic pawl 518 cools, its free end pushes the tooth, and hence the wheel 520 forward (clockwise). When the wheel 520 rotates clockwise, the display wheel 516 likewise rotates to display a new number. Having the benefit of the above disclosure, it will be apparent to those skilled in the art how this embodiment differs from the embodiments disclosed above. For simplicity, some of the similar features of this embodiment have not been shown in the drawing, but it will be appreciated that a window, locking pin, missing tooth, etc. can and would be applied to this embodiment as well.

Figure 7:
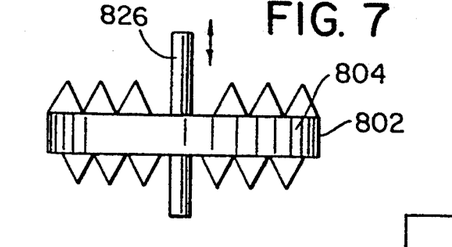
FIG. 7 is a side elevation schematic view of a sealed gas aneroid bellows actuator.

FIG. 5 shows yet another type of ratchet wheel for incremental rotation of a display surface. In this embodiment, the ratchet wheel 616 operates according to principles similar to an escapement wheel in a clock. The wheel 616 is provided with exterior teeth 630 and preferably is biased in a counterclockwise direction by a main spring 621 coupled to a hub 620. Rotation of the wheel is prevented by a first pawl 624 which rests against the shoulder 629 of a tooth 630 and which is biased by a pawl biasing spring 622. First pawl 624 is pivotally coupled with a spaced apart second pawl 625. An impulse or reciprocating connection 626 allows an impulse or reciprocating member such as a piston (examples of which are described below with reference to FIGS. 6 and 7) to move second pawl 625 towards the wheel 616. When second pawl 625 is moved towards the wheel 616, its coupling with the first pawl 624 about the pivot 623 causes the first pawl 624 to move away from wheel 616, thereby compressing spring 622. Pawls 624 and 625 are dimensioned and placed relative to wheel 616 such that as pawl 624 is moved away from the wheel, the wheel under action of main spring 621 is permitted to advance one half an increment (e.g., typically one-half tooth or one full) until it is stopped by the second pawl 625 which engages the shoulder 629 of another tooth 630. When the force applied to connection 626 is released, the spring 622 acts to move the first pawl 624 towards the wheel, thereby pivotally moving second pawl 625 away from the wheel. The wheel is thus permitted to advance another half increment in the interval between pawl 625 disengaging a tooth and pawl 624 engaging a tooth. With the benefit of the disclosure herein, those skilled in the art will appreciate how this embodiment of an incremental advancement device can be applied to the display described above. It will also be appreciated that if the pawls 624 and 625 are carefully dimensioned, spring 621 can be omitted since pawl 625 will engage a tooth 630 on its sloping side 628 and cause the wheel 616 to turn as the side 628 moves up out of the way of pawl 625. When pawl 624 then engages the slping side 628 of an adjacent tooth, a similar action will be effected until the wheel is advanced one tooth. In order to incorporate this device in a temperature cycle counter, it is only necessary to supply a temperature responsive device which will apply the impulsive force to connection 626. FIGS. 6 and 7 which are discussed in detail hereinafter, show two embodiments of temperature responsive devices which can supply an impulse or reciprocating force to the connection 626. One notable feature of this embodiment is that the display is incremented only after a full cycle of heating and cooling.

It should also be noted that if the heat responsive device coupled to 626 is a bidirectional or reciprocating device (pushes and pulls rather than only impulse pushing), the springs 621 and 622 may be omitted. With a bidirectional heat responsive device, when the device is heated and force is supplied to connection 626, thereby pushing second pawl 625 towards sloping surface 628 of a tooth 630. As the second pawl 625 engages the sloping surface of the tooth 630, it rides along the surface and advances the wheel 616 one half an increment. As the second pawl 625 engages the sloping surface 628, the first pawl 624 disengages shoulder 629 of the next counter-clockwise adjacent tooth, thereby freeing the wheel 616 to be advanced by the second pawl 625. When the bidirectional heat responsive device is cooled, a pulling force is applied to connection 626 and, through pivot 623, the first pawl 624 is pushed towards wheel 616 to engage a sloping surface 628 and advance the wheel 616 another half an increment. The alternating action of pawls 624 and 625 advance the wheel and prevent it from turning backwards.

It should be appreciated that the escapement mechanism described with reference to FIG. 6 is not limited to the advancement of the wheel by one half an increment. Thus, during the heating, the advancement can be from a small part of an increment to an almost complete increment, with the remainder being provided during cooling. Also, an "increment" should not be interpreted as a single tooth, as depending upon the placement of the indicia, an "increment" may comprise one, two, or a different number of teeth.

FIG. 6 shows a temperature responsive force supplier which might be used with the escapement mechanism of FIG. 5. The force supplier of FIG. 6 includes a container 702 filled with wax 704 which opens to a cylinder 706 containing a piston 708 therein. A piston rod 726 is coupled to piston 708 at one end and may be coupled to the connection 626 of FIG. 6 at its other end. When heated, the wax 704 melts and expands into the cylinder 706, thereby forcing piston 708 and thus piston rod 726 outward. When the wax cools, it contracts and flows back from the cylinder 706 into the container 702, thereby allowing piston 708 and piston rod 726 to return to their initial position. As aforementioned, it will be appreciated by those skilled in the art how this temperature responsive device can be used to actuate the escapement device of FIG. 5.

Figure 7A:
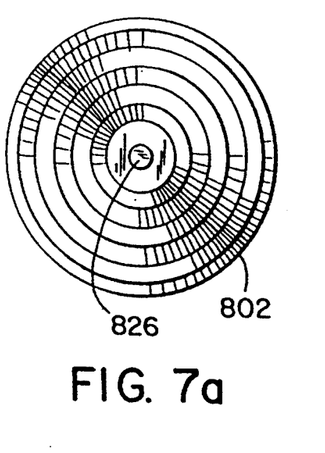
FIG. 7a is a top plan view of the actuator of FIG. 7.

FIGS. 7 and 7a show a sealed aneroid bellows 802 containing a gas 804 and coupled to a plunger 826. When heated, the gas 804 in the bellows 802 expands to move the plunger 826 outward, and when the gas cools, the gas contracts in the bellows 802 moving the plunger 826 inward. It will be appreciated by those skilled in the art how this temperature responsive device can be used to actuate the escapement device of FIG. 6, and how spring 622 of the escapement device may be eliminated.

Figure 8:
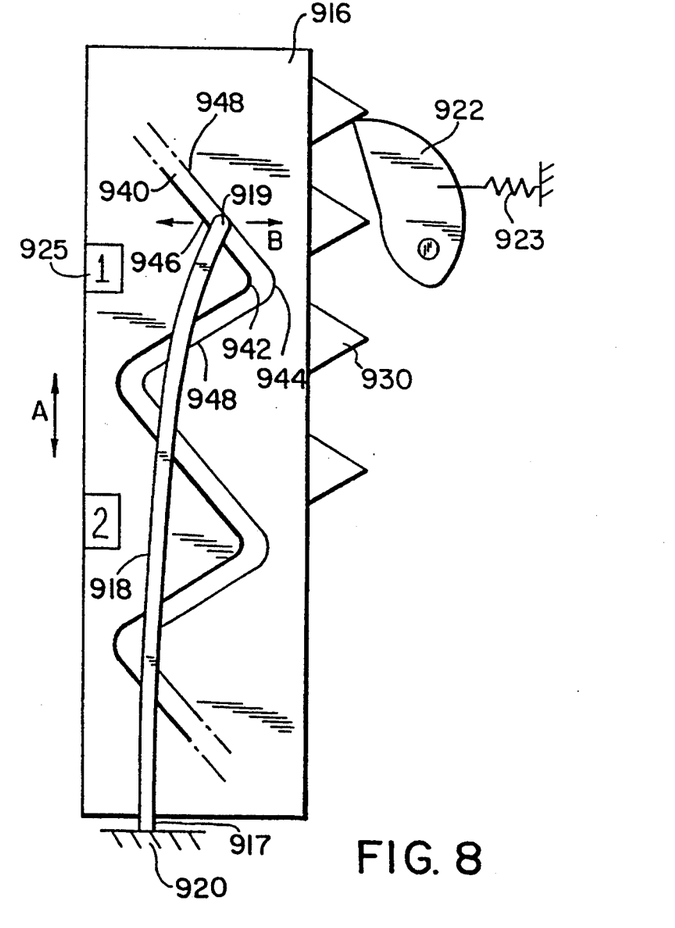
FIG. 8 is a side elevation schematic view of a slotted strip ratchet member driven by a bimetallic element.

FIG. 8 shows a different embodiment of a ratchet member advanced by a bimetallic member. Here, the ratchet member is not a wheel, but a strip 916 which moves up or down as shown by arrows A in FIG. 8. The strip 916 is provided with a "zigzag" slot 940 which is engaged by the free end 919 of a bimetallic member 918. Bimetallic member 918 is fixed to stationary coupling 920 at its other end 917 and is designed to bend toward the right as shown by the arrow B in FIG. 8 when it is heated, and return upright when cooled. A direction limiting pawl 922 biased by a spring 923 engages teeth 930 on a side of the strip 916 so that the strip may be advanced in only one direction; in this case up. Indicia 925 are provided on the strip for the same purpose as described above with reference to FIGS. 1–3. The slot 940 is dimensioned with walls 946, 948 and bends 942, 944 so that sideways movement of the bimetallic member 918 advances the strip through the engaging action of free end 919 biasing walls 946, 948. For example, when heated, the bimetallic member 918 bends to the right, with its free end 919 engaging wall 948, and causes strip 916 to move up against the pawl 922 which prevents downward movement of the strip while allowing upward movement. The bimetallic member 918 continues its rightward bend until it engages turn 944 in the slot 940 whereupon it can move no further. Upon cooling, the bimetallic member 918 starts straightening so that its free end 919 engages wall 946 of slot 940. By placing bend 942 higher than bend 944, the engagement of wall 946 by free end 919 of bimetallic member 918 causes the strip 916 to advance further. The movement of strip 916 further upwards continues until the bimetallic member 918 straightens completely and locates itself in the next bend. It is of note, that as with the escapement embodiment described above, this embodiment has the feature that the display is incremented only after a full cycle of heating and cooling.

Figure 9:
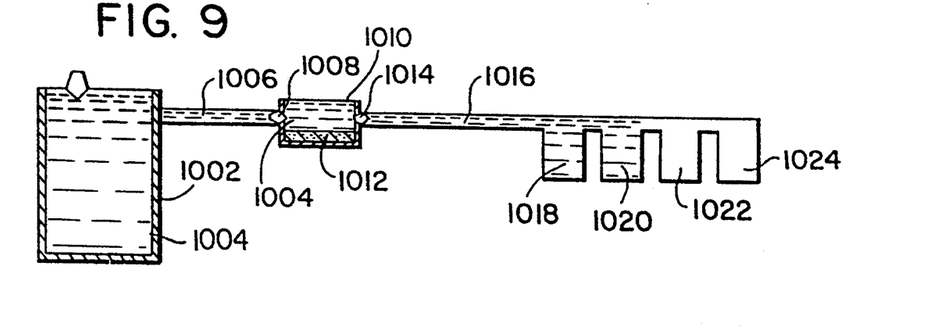
FIG. 9 is a side elevation schematic view of a fluid vessel indicator.
Figure 10:
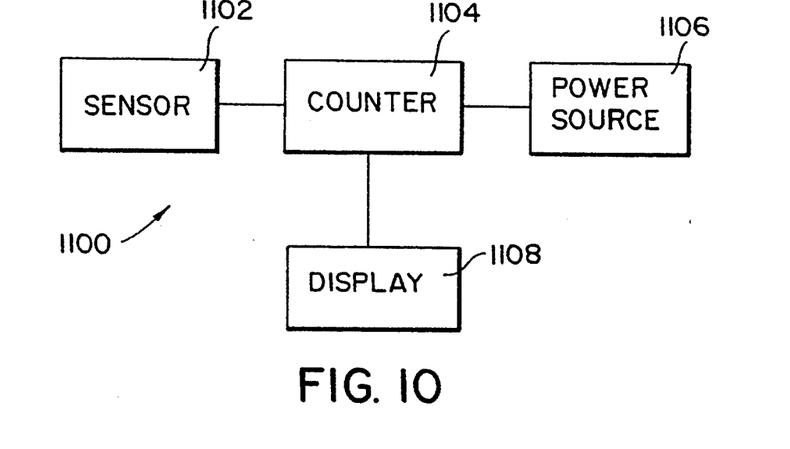
FIG. 10 is a schematic block diagram of an electronic temperature cycle counter.

FIG. 9 shows an apparatus for counting heating cycles which utilizes fluid mechanics and does not increment via a mechanical mechanism. The embodiment of FIG. 9 includes a fluid container 1002 containing a fluid 1004. Container 1002 is coupled to a measuring reservoir/pump 1010 by a conduit 1006 and a one-way valve 1008 which allows fluid 1004 from container 1002 to enter the reservoir 1010 through conduit 1006 but prevents fluid 1004 from exiting reservoir/pump 1010 through conduit 1006. The reservoir/pump is preferably a container which includes a self-contained expanding bottom pump portion containing wax 1012 or the like. In this manner, the bottom pump portion expands when heated. The reservoir/pump 1010 is further coupled to a conduit 1016 through a second one-way valve 1014 which allows fluid 1004 to flow from the reservoir 1010 into the conduit 1016. The conduit 1016 is coupled to a series of indicator fluid containers 1018, 1020, 1022, 1024, which are located sequentially downstream along the conduit 1016.

In use, when the medical instrument with the heat cycle counter of FIG. 9 is heated, the wax in the pump portion of reservoir/pump 1010 expands and forces whatever fluid was located in the reservoir portion of the reservoir/pump 1010 past one-way valve 1014 and into the fluid conduit 1016. By providing enough fluid in the reservoir of reservoir/pump 1010, one of the indicator fluid containers 1018 will at least partially fill and indicate a first use of the medical instrument. When the medical instrument cools, one-way valve 1014 prevents the fluid from returning into the reservoir of the reservoir/pump 1010. However, so that a vacuum is not formed in the reservoir of the reservoir/pump, fluid 1004 from the container 1002 will be provided through conduit 1006 and valve 1008. If desired, in order to guarantee flow from the container 1002 into the reservoir/pump, the container 1002 may be provided with a piston (not shown) which is subject to the ambient. It will be appreciated that the dimensions of the containers, reservoir, and conduits, as well as the volume of fluid in the apparatus are chosen so that fluid exiting reservoir/pump 1010 is sufficient to fill only one indicator container. Therefore, each time the medical instrument is heated to the appropriate temperature, the pump 1010 pumps enough fluid so that the next downstream indicator container 1020, 1022, 1024, etc is filled. It will also be appreciated that depending on the dimensions of the conduits and the volume of fluid, the indicator containers 1020, 1022, 1024 may be omitted and the conduit may simply be marked with use indicia similar to thermometer tube markings.

FIGS. 10, 11a, 11b and 11c show an electronic embodiment of the invention; i.e., an electronic temperature cycle counter 1100. The electronic temperature cycle counter 1100 shown schematically in FIG. 10 generally includes a sensor 1102 such as a thermistor, diode, transistor, integrated circuit (IC) or the like which is sensitive to changes in temperature, and which changes its electrical properties in response to changes in temperature. The sensor is coupled to an electronic counting circuit 1104 which in turn is coupled to a power source 1106 and a display 1108 such as an LCD. The counting circuit 1104 may be an integrated circuit combining a counter and an LCD driver or a microprocessor. The power source 1106 is ideally a "coin cell" (carbon-zinc, silver-oxide, lithium-iodide, etc.). The LCD display 1108 may be either a seven segment numeric display or a special symbol display. In one embodiment of the invention, the counter circuit 1104 is designed to register a change in the display after the sensor senses a "temperature excursion" i.e., a change in temperature from a preset low temperature to a preset high temperature and back to the low temperature. However, in another embodiment of the invention, if an oscillator is used in conjunction with the counter circuit (or microprocessor), the counter circuit 1104 can be arranged to register the amount of time the device has been above and/or below a predetermined temperature. This embodiment might be particularly useful for candles where the candles might melt together if left for a certain amount of time at a certain temperature. This embodiment might also be useful for milk, milk products, plastic products, etc. A flow chart for a counter circuit or microprocessor which performs this function is seen in FIG. 12. In even another embodiment of the invention, with particular application to milk and similar types of items, not only may the counter circuit 1104 keep track of cycles, but different threshold temperatures might be utilized to keep track of the useful life of the milk before it is spoiled. This embodiment is described in more detail hereinafter with reference to FIG. 12.

Figure 11A:
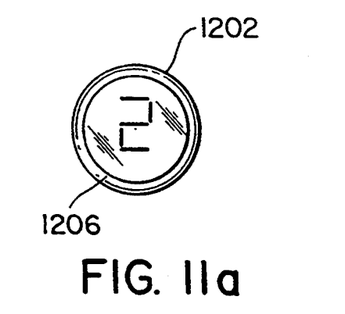
FIG. 11a is a front view of a packaged electronic temperature cycle.
Figure 11B:
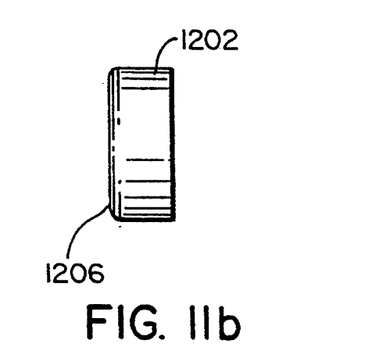
FIG. 11b is a side view of a packaged electronic temperature cycle counter.
Figure 11C:
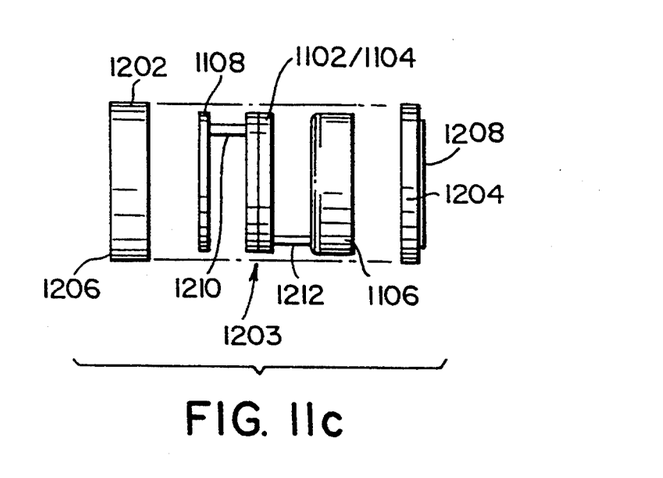
FIG. 11c is an exploded side elevation view of a packaged electronic temperature cycle counter.
Figure 12:
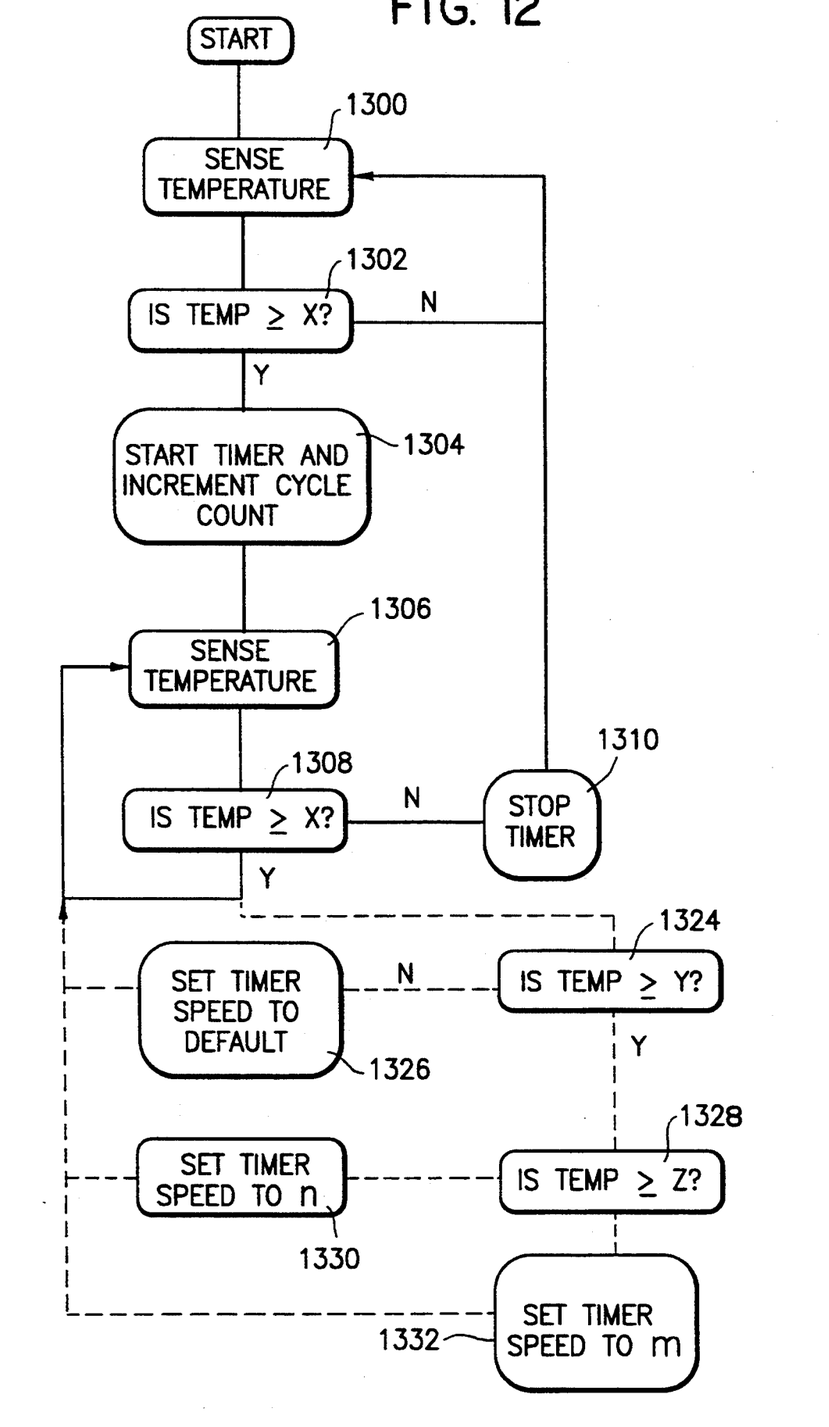
FIG. 12 is a flow chart of preferred programmings of the packaged electronic temperature cycle counter of FIGS. 10, and 11a–11c according to one embodiment of the invention.

FIGS. 11a–11c show a preferred packaging of the electronic temperature cycle counter 1100. A generally cylindrical container 1202 contains a sandwich of the LCD 1108, a miniature circuit board 1203 containing both the sensor 1102 and the counter circuit 1104, and the power cell 1106. The container is open faced with a retaining rim 1206 against which a self-contained LCD display disk 1108 is secured within the container. The circuit board 1203 containing both the sensor and the counter circuit is dimensioned to approximately the same diameter as the display disk and packed behind the display in the cylindrical container 1202. The display is coupled to the circuit board by wire connectors 1210, but may be connected in other ways such as biased contacts which couple when the pieces are pressed together, or directly by soldering. A disk shaped power cell 1106 is likewise packed behind the circuit board, and the power cell is also coupled to the circuit board by wire connectors 1212 as shown or in other ways known to those skilled in the art. The entire sandwich of the LCD, circuit board 1203, and power cell 1106 is enclosed within the cylindrical container 1202 by a rear cover 1204 which screws in place. The outside of the rear cover is preferably provided with a peel-and-stick self-adhesive strip 1208 so that the counter may be affixed to a temperature sensitive product, or a package or crate or other carrier means containing or carrying the product.

Turning to FIG. 12, a flow chart for a microprocessor or counting circuit is seen. At 1300, the temperature sensed by the sensor 1102 is read. At step 1302, the circuit determines whether the temperature is greater than a predetermined value X (e.g., 40° F. for milk). If not, the program continues by checking the temperature at step 1300 again, and recycling through steps 1300 and 1302. If the temperature is greater than a predetermined value, at step 1304, a timer is set and a cycle counter is incremented. While the cycle counter is being incremented although a full cycle has not occurred, it should be appreciated that, if desired, a different program could wait until the temperature dropped below the predetermined value X before registering a cycle count. Regardless, at step 1306, the temperature sensed by sensor 1102 is read again. If the temperature is greater than value X, the program returns to step 1306, and recycles until the temperature drops below X. At that time, the timer is stopped at step 1310, and the program returns to step 1300. With the provided program, it will be appreciated that both the cycle count and cumulative amount of time the temperature exceeds the predetermined value X are followed.

According to another aspect of the invention, and as seen in the phantom lines of FIG. 12, the circuit or microprocessor may be further programmed. Thus, if the temperature exceeds the predetermined value X at step 1308, the program continues at step 1324 where the temperature is compared to a second value or threshold Y. If the temperature does not exceed value Y, at 1326, the timer speed is kept at its default value set at step 1304. The program then continues at step 1306 as previously described. However, if the temperature does exceed value Y, at then, at step 1328, a determination is made whether the temperature exceeds value Z. If not, (i.e., the temperature is greater than Y but less than Z), then at step 1330 the timer speed is reset to a new, typically higher speed n appropriate for temperature Y. This permits the apparatus to provide additional emphasis to different temperatures. For example, if the temperature of milk exceeds 40° F. its shelf life starts decreasing at one rate (e.g., it might be good for five days). However, if the temperature exceeds, e.g., 50° F. its shelf life might decrease at another rate (e.g., it might be good for one day). Thus, if the timer/counter is set to count down from a value of, e.g., ten days, then, after five days of forty degree treatment, the timer/counter might show no useful shelf life left. On the other hand, after two and one-half days at forty degrees, and half a day at fifty degrees, or one day of fifty degree treatment, the timer/counter would show no useful shelf life left.

Returning to FIG. 12, it will be appreciated that by providing additional threshold temperatures, additional timer speeds can be utilized. Thus, if at step 1328 it is determined that the temperature exceeded threshold temperature Z, then the timer is set to yet another rate (m) at step 1332, and the program countinues at step 1306. With the provided algorithm, it will be appreciated that when the temperature drops below temperature Z, then the timer will be set back to rate (n) at step 1330, and when the temperature further drops below temperature Y, the timer will be set back to its default at step 1326. Finally, when the temperature drops below temperature X, the timer will be stopped (at step 1310), and the program will continue at step 1300.

It will be appreciated that additional, and/or different thresholds could be utilized as desired, and that the output which is provided to the display could take various forms; e.g., shelf life left; a value from one to one hundred; etc. It will also be appreciated that the thresholds may be thresholds of increasing or decreasing temperatures. Further, it will be appreciated that means for resetting the apparatus may be provided so that if the entire apparatus may be reused with the same or a replacement battery.

There have been described and illustrated herein several embodiments of a temperature cycle counter. While particular embodiments of the invention have been described, it is not intended that the invention be limited thereto, as it is intended that the invention be as broad in scope as the art will allow and that the specification be read likewise. Thus, while particular incremental indicia in the form of numbers have been disclosed, it will be appreciated that other indicia could be utilized. For example, a color code could be used (e.g., a sequence of colors, or no color and then red, or all black then red, etc.), dots could be used, or the indicia could be in reverse order to indicate the number of temperature cycles available. In addition, instead of a number, the words "temperature damaged" might appear in the window, or a warning (e.g., "please discard" or a red marker, etc.) might appear in the window. Also, while certain configurations of a ratchet wheel have been shown, it will be recognized that other configurations could be used with similar results obtained. For example, the outer surface of the wheel could be either faceted or smoothly cylindrical or a combination of those. Moreover, while particular configurations have been disclosed in reference to teeth, it will be appreciated that other configurations could be used as well.

As to the bimetallic temperature responsive member, it will be appreciated that advancement of the indicia may be effected either upon heating or cooling or only upon a complete temperature excursion. Therefore, with the benefit of the instant disclosure, it will be understood how various features of the different embodiments could be combined to create yet additional embodiments. The bimetallic member may be used with the escapement ratchet or the impulse supplying devices described with reference to the escapement device may be applied to the other ratchet devices.

It will further be appreciated by those skilled in the art that in the escapement embodiment, it may be possible to provide different actuation means other than those shown and described. In addition, it will be appreciated that the terms "clockwise" and "counter clockwise" have relative meaning only and the ratchet wheels disclosed could be arranged to rotate in either direction. Furthermore, while the locking bore and locking pin have been disclosed as having a particular location and configuration, it will be understood that different types of locking means can achieve the same or similar function as disclosed herein.

In the fluid mechanical embodiment, it will be appreciated that the number of containers and the volume of fluid will depend on the number of temperature cycles to be counted. In the electronic embodiment, it will be appreciated that the exact circuitry and packaging of the counter may be varied according to need and/or economics. In particular, the counter circuit and the display driver circuit may be integrated or kept separate depending the economics of manufacture. The display may be a segmented numeric or alpha-numeric LCD display or any other suitable display having sequential indicia. Likewise, the programming of the circuit or microprocessor provided may take different forms to accomplish similar results and/or additional functions.

Finally, it will be appreciated that while certain applications were listed for the application of the temperature cycle counter, the temperature cycle counter can be utilized in many different applications. It will therefore be appreciated by those skilled in the art that yet other modifications could be made to the provided invention without deviating from its spirit and scope as so claimed.

We claim:

1. A apparatus for counting the number of times a selected temperature cycle has occurred, comprising:
   a) a cycle indicator, said indicator having a predetermined plurality of sequential indicia;
   b) temperature responsive means for indicating a next one of said indicia when said selected temperature cycle occurs; and
   c) initial actuation means for preventing said temperature responsive member from indicating next one of said indicia regardless of the occurrence of the selected temperature cycle until after said initial actuation means is triggered, wherein, after said initial actuation means is triggered, said temperature responsive means is not prevented by said initial actuation means from indicating a next one of said indicia each time the selected temperature cycle occurs.

2. A apparatus according to claim 1, further comprising:
   d) last indicia stop means for preventing said temperature responsive member from indicating a next one of said indicia beyond a predetermined last one of said indicia.

3. A apparatus according to claim 1, wherein:
   said cycle indicator comprises a ratchet member having a plurality of teeth, and
   said temperature responsive member comprises an advancing pawl means for engaging said teeth such that when said advancing pawl means is subjected to a substantial change in temperature said advancing pawl means moves said tooth a first distance to advance said ratchet member so that a next one of said incremental indicia is indicated.

4. A apparatus according to claim 1, wherein:
   said cycle indicator comprises a ratchet wheel having inner teeth and an outer display surface, said outer display surface containing said plurality of indicia, and
   said temperature responsive member comprises a bimetallic pawl engaging said teeth.

5. A apparatus according to claim 1, wherein:
   said temperature responsive member comprises a bimetallic element.

6. A apparatus according to claim 2, wherein:
   said cycle indicator comprises a ratchet wheel having a plurality of teeth,
   said temperature responsive member comprises a pawl engaging said teeth, and
   said last indicia stop means comprises a space between two adjacent teeth.

7. A apparatus according to claim 3, wherein:
   said actuation means comprises a removable pin, said actuation means being triggered by removing said pin.

8. An apparatus according to claim 3, further comprising:
   d) blocking pawl means for engaging said ratchet member so as to allow movement of said ratchet member in one direction only.

9. A apparatus according to claim 8, wherein:
   said ratchet member is a ring.

10. A apparatus according to claim 9, wherein:
    said teeth are located on an interior surface of said ring and said display surface is located on an exterior surface of said ring.

11. A apparatus according to claim 9, wherein:
    said incremental indicia comprise a plurality of sequentially numbered facets on an exterior surface of said ring.

12. A apparatus according to claim 8, further comprising:
    e) masking means for masking a plurality of said indicia and allowing an indicated indicator to be seen, wherein
    said masking means comprises a housing with a window.

13. A apparatus according to claim 12, wherein:
    said housing comprises a ferrule.

14. A apparatus according to claim 8, wherein:
    said temperature responsive advancing pawl means is a curved bimetallic member which engages a shoulder of a tooth of said ratchet member and expands at least aid first distance when heated a first amount, thereby moving said ratchet member during heating, and contracts at least said first distance when cooled said first amount.

15. A apparatus according to claim 8, wherein:
    said temperature responsive advancing pawl means is a curved bimetallic member which expands at least said first distance when heated a first amount, and engages a shoulder of a tooth of said ratchet member and contracts at least said first distance when cooled said first amount, thereby moving said ratchet member during cooling.

16. An apparatus according to claim 8, further comprising:
    d) movement limiting means for limiting movement of said advancing pawl means, wherein
    said advancing pawl means is a curved bimetallic member which expands when heated, and contracts when cooled, wherein said movement limiting means limits movement of said curved bimetallic member to approximately said first distance upon heating and cooling.

17. An apparatus according to claim 16, wherein:
    said movement limiting means comprises a hub means for holding one end of said curved bimetallic member, said hub means having a key extending from said hub, said key engaging said curved bimetallic member to limit movement of said bimetallic member to approximately said first distance upon heating and cooling.

18. An apparatus according to claim 16, wherein:
said movement limiting means comprises a first stop means for limiting movement of said curved bimetallic member upon heating, and a second stop means for limiting movement of said curved bimetallic member upon cooling.

19. A apparatus according to claim 8, wherein:
said initial actuation means comprises removable locking means engaging said ratchet member to prevent movement of said ratchet member by said temperature responsive advancing pawl means until removed.

20. A apparatus according to claim 19, wherein:
said removable locking means comprises a locking pin and said ratchet member includes a bore for receiving said pin.

21. A apparatus according to claim 8, wherein:
said teeth number at least one less than said plurality of incremental indicia such that upon advancing said ratchet member to a last one of said incremental indicia said advancing pawl means no longer engages a tooth and said ratchet member can no longer be advanced by said advancing pawl means.

22. An apparatus according to claim 1, wherein:
said cycle indicator comprises a rotating member having an outer surface displaying said sequential indicia, and
said temperature responsive means comprises
a stationary ratchet member and
a bimetallic pawl having a fixed end and a free end, said fixed end coupled to said cycle indicator, and said free end engaging said ratchet member.

23. An apparatus according to claim 1, wherein:
said cycle indicator comprises a rotating member having an outer surface displaying said sequential indicia, and a toothed axle, and
said temperature responsive means comprises a bimetallic pawl having a fixed end and a free end, said free end engaging said toothed axle.

24. An apparatus according to claim 1, further comprising:
d) an escapement mechanism having a gear coupled to said cycle indicator and having an advancement mechanism coupled to said temperature responsive means.

25. An apparatus according to claim 24, wherein:
said temperature responsive means comprises an aneroid bellows.

26. An apparatus according to claim 24, wherein:
said temperature responsive means comprises a cylinder and a piston, said cylinder containing a temperature responsive medium whereby heating and cooling of said medium causes movement of said piston.

27. An apparatus according to claim 1, wherein:
said cycle indicator comprises a fluid conduit which receives fluid, and
said temperature responsive means comprises a fluid supply with said fluid, and a temperature responsive pump means, with said pump means coupled to said fluid conduit, and said fluid supply coupled to said temperature responsive pump means, wherein when said apparatus is heated, said temperature responsive pump means pumps said fluid into said fluid conduit, and when said apparatus is cooled said fluid supply supplies additional fluid to said temperature responsive pump means.

28. An apparatus according to claim 27, wherein:
said temperature responsive means further comprises first and second valve means, said first valve means coupled between said fluid supply and said temperature responsive pump means for preventing fluid received by said temperature responsive pump means from reentering said fluid supply, and said second valve means coupled between said temperature responsive pump means and said fluid conduit for preventing fluid received by said fluid conduit from reentering said temperature responsive pump means.

29. An apparatus according to claim 28, wherein:
said cycle indicator further comprises a plurality of containers sequentially coupled to said fluid conduit, said plurality of containers sequentially receiving fluid pumped by said temperature responsive fluid pump means.

30. An apparatus according to claim 29, wherein:
said temperature responsive pump means includes a measuring reservoir which holds precisely enough of said fluid such that when said temperature responsive fluid pump means pumps the fluid in said measuring reservoir, an additional container is substantially filled.

31. An apparatus according to claim 1, wherein:
said cycle indicator comprises a strip with a zigzag slot, and
said temperature responsive means comprises a bimetallic member having a fixed end and a free end, said free end engaging said zigzag slot.

32. An apparatus according to claim 31, wherein:
said cycle indicator further comprises a plurality of teeth, and a direction limiting pawl engaging said teeth.

33. An apparatus according to claim 1, further comprising:
d) a power supply means, wherein
said cycle indicator comprises an electronic display and an electrical circuit means for driving said display, and
said temperature responsive means comprises an electronic temperature sensor coupled to said electrical circuit means, and
said power supply means is coupled to and powers said electronic display, said electrical circuit means, and said electronic temperature sensor means.

34. An apparatus according to claim 33, wherein:
said electronic display comprises an LCD.

35. An apparatus according to claim 33, wherein:
said electronic temperature sensor comprises a device selected from the group consisting of a thermistor, a diode, a transistor, and an integrated circuit.

36. An apparatus according to claim 33, wherein:
said electrical circuit means and said electronic temperature sensor means are provided on a single circuit board.

37. An apparatus according to claim 33, wherein:
said electrical circuit means for driving said display further comprises a microprocessor.

38. An apparatus according to claim 33, wherein:
said power cell is a coin cell selected from the group consisting of carbon-zinc, silver oxide, and lithium-iodide.

39. An apparatus according to claim 33, further comprising:
   e) a housing containing said electronic display, said electronic temperature sensor, said electrical circuit means, and said power supply means.

40. An apparatus according to claim 39, further comprising:
   f) adhesive means on said housing for attaching said housing to said instrument.

41. An apparatus according to claim 39, wherein:
   said housing comprises a cylinder with an open face and a removable back.

42. An apparatus according to claim 33, wherein:
   said electronic display comprises an LCD,
   said electronic temperature sensor comprises a device selected from the group consisting of a thermistor, a diode, a transistor, and an integrated circuit,
   said electrical circuit means and said electronic temperature sensor means are provided on a single circuit board,
   said electrical circuit means for driving said display further comprises a microprocessor, and
   said power cell is a coin cell selected from the group consisting of carbon-zinc, silver oxide, and lithium-iodide.

43. An apparatus according to claim 33, wherein:
   said electrical circuit means comprises timing means for timing the length of time said temperature sensor exceeds a first threshold temperature.

44. An apparatus according to claim 33, wherein:
   said electrical circuit means comprises timing means for timing the length of time said temperature sensor senses a temperature below a first threshold temperature.

45. An apparatus according to claim 43, wherein:
   said electrical circuit means comprises means for determining the length of time said temperature sensor senses a temperature exceeding a second threshold temperature, said second threshold temperature being higher than said first threshold temperature, and
   said electrical circuit means further comprises means for adjusting a rate of said timing means when said temperature sensor senses said temperature exceeding said second threshold temperature.

46. An apparatus for determining the length of time said apparatus has been exposed to a temperature exceeding or below a first predetermined threshold temperature, comprising:
   a) an electronic display means for displaying a length of time indication;
   b) an temperature sensor means for sensing the temperature to which said apparatus is exposed;
   c) an electrical circuit coupled to said temperature sensor means and coupled to said electronic display means, said electrical circuit including timing means for timing at a first rate a first cumulative length of time said apparatus has been exposed to a temperature exceeding or below said first predetermined threshold temperature, and said electrical circuit driving said electronic display means and causing said electronic display means to provide said indication based at least partially on said first cumulative length of time; and
   d) a power supply means coupled to said electronic display means and said electrical circuit for powering said electronic display means and said electrical circuit.

47. An apparatus according to claim 46, wherein:
   said electrical circuit times a second cumulative length of time said apparatus has been exposed to a temperature above or below a second predetermined threshold temperature, wherein said timing means times at a second rate said second cumulative length of time, and wherein said electronic display means provides said indication based also at least partially on said second cumulative length of time.

48. An apparatus according to claim 47, wherein:
   said electrical circuit times a third cumulative length of time said apparatus has been exposed to a temperature above or below a third predetermined threshold temperature, wherein said timing means times at a third rate said second cumulative length of time, and wherein said electronic display means provides said indication based also at least partially on said third cumulative length of time.

49. An apparatus according to claim 48, further comprising:
   housing means for housing said electronic display means, said temperature sensor means, said electrical circuit, and said power supply means, said housing means including a window for seeing said electronic display means, wherein
   said electronic display means is an LCD display,
   said temperature sensor means comprises a device selected from a group consisting of a thermistor, a diode, a transistor, and an integrated circuit, and
   said power cell is a coin cell.

* * * * *